United States Patent [19]

Takamatsu et al.

[11] Patent Number: 5,633,366

[45] Date of Patent: May 27, 1997

[54] PYRIMIDINE NUCLEOSIDE DERIVATIVES AND METHODS FOR PRODUCING THEM

[75] Inventors: Satoshi Takamatsu; Hiroshi Shiragami; Yumiko Uchida; Kunisuke Izawa, all of Kawasaki, Japan

[73] Assignee: Ajinomoto Co., Inc., Tokyo, Japan

[21] Appl. No.: 285,697

[22] Filed: Aug. 4, 1994

[30] Foreign Application Priority Data

Aug. 4, 1993 [JP] Japan ................................. 5-193332
Aug. 1, 1994 [JP] Japan ................................. 6-180109

[51] Int. Cl.$^6$ ........................ C07H 1/00; C07H 19/067; C07H 19/073
[52] U.S. Cl. ............... 536/28.4; 536/28.1; 536/28.5; 536/28.51; 536/28.52; 536/28.53; 536/28.54; 536/28.55; 536/115; 536/124; 536/127
[58] Field of Search ..................... 536/28.1, 28.4, 536/28.5, 28.52, 28.53, 28.54, 28.55, 115, 124, 127

[56] References Cited

U.S. PATENT DOCUMENTS

| | | | |
|---|---|---|---|
| 3,539,550 | 11/1970 | Greenberg et al. | 536/28.5 |
| 3,870,700 | 3/1975 | Kotick et al. | 536/28.53 |
| 3,873,516 | 3/1975 | Kotick et al. | 536/28.5 |
| 4,681,933 | 7/1987 | Chu et al. | 536/28.54 |
| 4,762,823 | 8/1988 | Watanabe et al. | 514/50 |
| 4,914,233 | 4/1990 | Freskos et al. | 536/27.11 |
| 4,965,374 | 10/1990 | Chou et al. | 536/27.6 |
| 5,310,895 | 5/1994 | Shiragami et al. | |
| 5,336,770 | 8/1994 | Shiragami et al. | |

FOREIGN PATENT DOCUMENTS

| | | |
|---|---|---|
| 0 280 128 | 8/1988 | European Pat. Off. . |
| 0 292 101 | 11/1988 | European Pat. Off. . |
| 0 325 537 | 7/1989 | European Pat. Off. . |
| 0 470 355 | 2/1992 | European Pat. Off. . |
| 0 519 464 | 12/1992 | European Pat. Off. . |
| 2 224 380 | 11/1973 | Germany . |
| 279 247 | 5/1990 | Germany . |

OTHER PUBLICATIONS

Chemical Abstracts, vol. 95, No. 13, 1981, AN–115951q, CS–184,526, Aug. 15, 1980.
Chemical Abstracts, vol. 85, No. 9, 1976, AN–63304c, JP–76–36467, Mar. 27, 1976.
Chemical Abstracts, vol. 109, No. 11, 1988, AN–93541j, HU 43,615, Nov. 30, 1987.

*Primary Examiner*—James O. Wilson
*Attorney, Agent, or Firm*—Oblon, Spivak, McClelland, Maier & Neustadt, P.C.

[57] ABSTRACT

Nucleoside derivatives such as 2'-deoxy-2'-bromo-5'-O-acetyl-5-methyluridine, etc., are important intermediates which can be converted into nucleoside derivatives, such as 3'-azido-3'-deoxythymidine, etc., which are useful as medicines.

5 Claims, No Drawings

PYRIMIDINE NUCLEOSIDE DERIVATIVES AND METHODS FOR PRODUCING THEM

BACKGROUND OF THE INVENTION

1. Field of the Invention

The present invention relates to novel methods for producing 3'-azido-3'-deoxythymidine (azidothymidine, AZT, zidovudine), which is useful as an antiviral agent, and its related compounds. The present invention also relates to novel intermediates useful in such a method.

2. Discussion of the Background

It has been reported that 3'-azido-3'-deoxythymidine exhibits a strong anti-viral activity against human immunodeficiency viruses (HIVs) and is noticeably effective for treating acquired immune deficiency syndrome (AIDS) (R. Yarchoan et al., *The Lancet*, 1(8481), pp. 575–580, Mar. 15, 1986). At present, therefore, the compound is used for treating AIDS and AIDS-related complex (ARC).

To produce 3'-azido-3'-deoxythymidine on a laboratory scale, there are two known methods. One method uses thymidine as a starting material and introduces an azido group into the 3'-position of thymidine (R. Glinski et al., *J. Chem. Soc. D*, (15), pp. 915–916, 1970; R. Glinski et al., *J. Org. Chem.*, 38(25), pp. 4299–4305, 1973); and the other method involves linking a sugar moiety into which an azide group has been introduced to the base moiety of a nucleic acid (N. Dyatkina et al., *Bioorg. Khim.*, 12(8), pp. 1048–1053, 1986; G. Fleet et al., *Tetrahedron Lett.*, 28 (31), pp. 3615–3618, 1987; G. Fleet et al., *Tetrahedron*, 44 (2), pp. 625–636, 1988; C. Chu et al., *Tetrahedron Lett.*, 29 (42), pp. 5349–5352, 1988). The former method may be put into industrial application but has a problem in that it uses thymidine, which is high-priced and is difficult to obtain on an industrial scale, as the starting material. In the latter method, the production of the sugar moiety into which an azido group has been introduced is difficult and, in addition, both α- and β-isomers are produced when the saccharide moiety is linked to the base moiety of a nucleic acid moiety so that they must be separated from each other. For these reasons, it is difficult to say that the latter method is industrially useful.

Thus, there remains a need for a method of producing 3'-azido-3'-deoxythymidine and related compounds, which does not use expensive and scarce starting materials, does not involve the separation of α- and β-isomers, and is useful on an industrial scale.

SUMMARY OF THE INVENTION

Accordingly, it is one object of the present invention to provide novel methods for producing 3'-azido-3'deoxythymidine and related compounds.

It is another object of the present invention to provide methods for producing 3'-azido-3'-deoxythymidine and related compounds which are useful on an industrial scale.

It is another object of the present invention to provide industrially useful methods for producing 3'-azido-3'-deoxythymidine and related compounds, which do not use thymidine, which is high-priced and is difficult to obtain in a large amount, as a starting material.

It is another object of the present invention to provide methods for producing 3'-azido-3'-deoxythymidine and related compounds which do not require separation of α- and β-isomers.

It is another object of the present invention to provide novel intermediates which are useful in such methods.

These and other objects which will become apparent during the following detailed description, have been achieved by the inventors discovery that 5-methyluridine may be used as a starting material to afford 5'-protected thymidines which are intermediates that can be easily converted into 3'-azido-3'-deoxythymidine and its related compounds.

Specifically, the present invention provides compounds of formula (I), which are intermediates which can be converted into 3'-azido-3'-deoxythymidine and its related compounds.

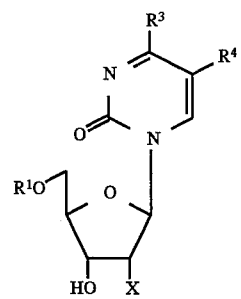

wherein X represents a halogen atom; $R^1$ represents a hydrogen atom, a hydrocarbon group having 1 to 19 carbon atoms, an acyl group having 1 to 7 carbon atoms, or an organic silyl group; $R^3$ represents a hydroxy group, a protected hydroxyl group, an amino group, or a protected amino group; and $R^4$ represents a hydrocarbon group having 1 to 12 carbon atoms, a hydrogen atom or a halogen atom.

The present invention also provides a method for producing compounds of formula (I), by reacting a compound of formula (III):

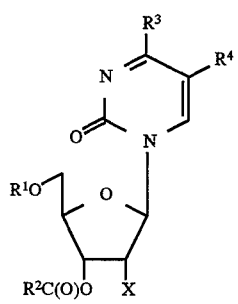

wherein X represents a halogen atom; $R^1$ represents a hydrogen atom, a hydrocarbon group having 1 to 19 carbon atoms, an acyl group having 1 to 7 carbon atoms, or an organic silyl group; $R^2$ represents an alkyl group having 1 to 6 carbon atoms; $R^3$ represents a hydroxyl group, a protected hydroxyl group, an amino group, or a protected amino group; and $R^4$ represents a hydrocarbon group having 1 to 12 carbon atoms, a hydrogen atom or a halogen atom, with a weak base.

The present invention further provides a method for producing compounds of formula (VII):

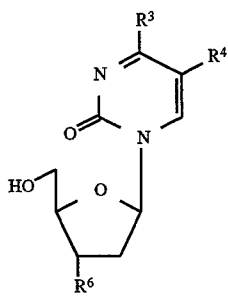

wherein $R^3$ represents a hydroxyl group, a protected hydroxyl group, an amino group, or a protected amino group; $R^4$ represents a hydrocarbon group having 1 to 12 carbon atoms, a hydrogen atom or a halogen atom; and $R^6$ represents an azido group, a cyano group or a fluoro group, by reducing a compound of formula (I) with a palladium catalyst or a nickel catalyst in the presence of a hydrogen donor, to give a compound of formula (IV):

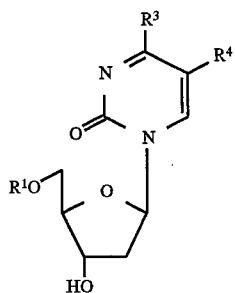

wherein $R^1$ represents a hydrogen atom, a hydrocarbon group having 1 to 19 carbon atoms, an acyl group having 1 to 7 carbon atoms, or an organic silyl group; $R^3$ represents a hydroxyl group, a protected hydroxyl group, an amino group, or a protected amino group; and $R^4$ represents a hydrocarbon group having 1 to 12 carbon atoms, a hydrogen atom or a halogen atom, then reacting the compound of formula (IV) with a sulfonyl halide to give a compound of formula (V):

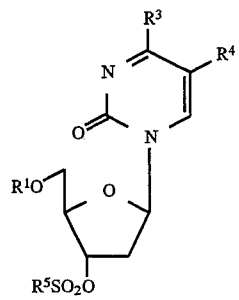

wherein $R^1$ represents a hydrogen atom, a hydrocarbon group having 1 to 19 carbon atoms, an acyl group having 1 to 7 carbon atoms, or an organic silyl group; $R^3$ represents a hydroxyl group, a protected hydroxyl group, an amino group, or a protected amino group; $R^4$ represents a hydrocarbon group having 1 to 12 carbon atoms, a hydrogen atom or a halogen atom; and $R^5$ represents an aryl group, an alkyl group, or a haloaralkyl group, the subjecting the compound or a formula (V) to ring-closure in the presence of a base to give a compound of formula (VI):

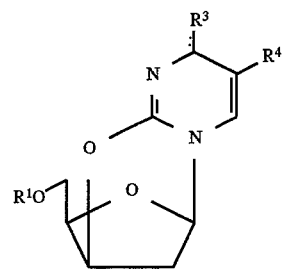

wherein $R^1$ represents a hydrogen atom, a hydrocarbon group having 1 to 19 carbon atoms, an acyl group having 1 to 7 carbon atoms, or an organic silyl group; $R^9$ represents an oxygen atom (when the symbol $=$ is a double bond), a protected hydroxyl group (when the symbol $=$ is a single bond), an amino group (when the symbol $=$ is a single bond), or a protected amino group (when the symbol $=$ is a single bond); and $R^4$ represents a hydrocarbon group having 1 to 12 carbon atoms, a hydrogen atom or a halogen atom, and subjecting the compound of formula (VI) to ring-cleavage with an azide, a cyanide or a fluoride and removing the hydroxyl-protective group $R^1$ at the 5'-position in the formula before or after the ring-cleavage.

DETAILED DESCRIPTION OF THE PREFERRED EMBODIMENTS

As one typical example of the above-mentioned compounds of formula (I), mentioned is 2'-deoxy-2'-bromo-5'-O-acetyl-5-methyluridine. This compound is an important intermediate which may be converted into the above-mentioned 3'-azido-3' deoxythymidine of formula (VII).

Moreover, X in the above-mentioned compounds of formula (I) can be selected from a halogen atom. Examples of a halogen atom include fluorine, chlorine, bromine, iodine, etc. Bromine is preferred.

$R^5$ in the above-mentioned compounds of formula (I) can be a hydrogen atom, a hydrocarbon group having 1 to 19 carbon atoms, an acyl group having 1 to 7 carbon atoms, or an organic silyl group. Examples of a hydrocarbon groups having 1 to 19 carbon atoms include a methyl group, an ethyl group, an isopropyl group, an benzyl group, etc. Examples of an acyl group having 1 to 7 carbon atoms include an acetyl group, a benzoyl group, etc. Examples of an organic silyl group include a trimethylsilyl group, a t-butyldimethylsilyl group, etc.

$R^2$ can be an alkyl group having 1 to 6 carbon atoms, examples of which includes a methyl group, an ethyl group, an isopropyl group, a propyl group, a n-butyl group, a t-butyl group, an isobutyl group, a sec-butyl group, a n-pentyl group, an isopentyl group, a neopentyl group, a n-hexyl group, an isohexyl group, etc.

$R^3$ in the compounds of formula (I) can be a hydroxyl group, a protected hydroxyl group, an amino group, or a protected amino group. Examples of a protected hydroxyl group and a protected amino group include a trimethylsilyloxy group, a t-butyldimethylsilyloxy group, an acetyloxy group, a benzoyloxy group, a benzyloxy group, an acetylamino group, benzoylamino group, a benzylamino group, etc.

$R^4$ in the compounds of formula (I) can be a hydrocarbon group having 1 to 12 carbon atoms, a hydrogen atom. Examples of a hydrocarbon group having 1 to 12 carbon atoms include a methyl group, an ethyl group, an isopropyl group, a benzyl group, a vinyl group, an aryl group (phenyl, tolyl, xylyl, mesityl, naphthyl, benzyl, etc.), an ethynyl group, a 1-propynyl group, a 2-propynyl group, etc. Examples of a halogen atom include fluorine, chlorine, bromine, iodine, etc.

$R^5$ may be an aryl group (phenyl, tolyl, mesityl, xylyl, naphthyl, etc.), an alkyl group having 1 to 4 carbon atoms, or a halogenoalkyl group having 1 to 4 carbon atoms.

The above-mentioned are not intended to be limiting thereof.

Compounds of formula (III) such as typically 2'-deoxy-2'-bromo-3',5'-O-diacetyl-5-methyluridine, which are the starting materials of the present invention, may be produced according to the method disclosed in Japanese Patent Application No. 3-245290.

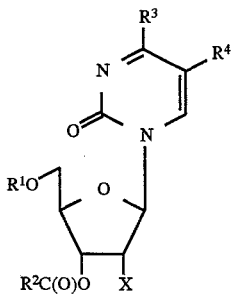
(III)

wherein X represents a halogen atom; $R^1$ represents a hydrogen atom, a hydrocarbon group having 1 to 19 carbon atoms, an acyl group having 1 to 7 carbon atoms, or an organic silyl group; $R^2$ represents an alkyl group having 1 to 6 carbon atoms; $R^3$ represents a hydroxyl group, a protected hydroxyl group, an amino group, or a protected amino group; $R^4$ represents a hydrocarbon group having 1 to 12 carbon atoms, a hydrogen atom or a halogen atom.

Precisely, the compounds of formula (III) may be obtained by reacting a compound, such as typically 5-methyluridine, of formula (VIII):

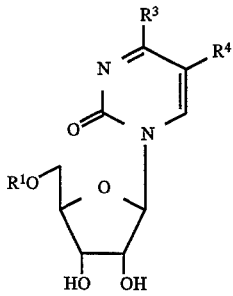
(VIII)

wherein $R^1$ represents a hydrogen atom, a hydrocarbon group having 1 to 19 carbon atoms, an acyl group having 1 to 7 carbon atoms, or an organic silyl group; $R^3$ represents a hydroxyl group, a protected hydroxyl group, an amino group, or a protected amino group; $R^4$ represents a hydrocarbon group having 1 to 12 carbon atoms, or a halogen atom, with an orthoester of an organic acid ($R^8C(OR^7)_3$), such as a trialkyl orthoacetate ($MeC(OR)_3$), etc., in acetic acid to convert it into a 2', 3'-O-alkoxyalkylidene compound of a general formula (IX):

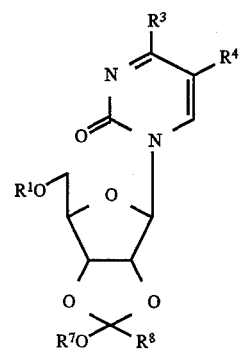
(IX)

wherein $R^1$ represents a hydrogen atom, a hydrocarbon group having 1 to 19 carbon atoms, an acyl group having 1 to 7 carbon atoms, or an organic silyl group; $R^3$ represents a hydroxy group, a protected hydroxyl group, an amino group, or a protected amino group; $R^4$ represents a hydrocarbon group having 1 to 12 carbon atoms, a hydrogen atom or a halogen atom; $R^7$ and $R^8$ each represent an alkyl group having 1 to 6 carbon atoms, then preferably concentrating the reaction mixture under reduced pressure, before or after the compound formed has been isolated from the mixture, and thereafter reacting it with a solution of a carboxylic acid containing a hydrogen halide, such as a solution of acetic acid containing hydrogen bromide, and/or a carboxylic acid halide such as acetylbromide.

The weak base used for producing the compound of formula (I) from the compound of formula (III) includes, for example, hydroxylamine, ammonia and their salts; primary to quaternary amines and their salts; metal hydroxides such as barium hydroxide, etc.; metal alkoxides such as sodium methoxide, potassium methoxide, etc.; lithium ammonia solution; basic ion-exchanging resins; carbonates such as potassium carbonate, sodium carbonate, sodium hydrogencarbonate, etc.; phosphates such as disodium hydrogenphosphate, etc.; acetates such as sodium acetate, etc.; dilute alkali solutions of sodium hydroxide, lithium hydroxide, etc. However, especially preferred is hydrazine monohydrate or triethylamine. Buffers that have been adjusted to have a suitable pH by suitable methods using the above-mentioned bases may also be used. The amount of the base to be used is suitably from 1 to 10 equivalents, preferably 1 to 5 equivalents, relative to the compound to be reacted with the base, but an excessive amount of the base may also be used with no problem. As the reaction solvent, suitable are alcohol solvents such as methanol, ethanol, etc., as well as acetonitrile, water, etc. The reaction system may be or may not be dewatered.

The reaction is effected at temperatures ranging from −40° C. to +40° C., preferably 0° to 20° C. The reaction time is not limited but depends on the reaction temperature and the amount of the base used. In general, good yields are obtained in from 0.5 to 120 hours. To isolate the compound formed, the base is neutralized with an acid such as hydrochloric acid, etc. or with an ion-exchanging resin, then the reaction mixture is concentrated, and thereafter the compound formed may be isolated by ordinary extraction using an organic solvent such as ethyl acetate, etc. After the reaction, the reaction mixture may be subjected to the next step for reduction, without isolating the product formed.

According to the present reactions which are described above, it is possible to achieve the selective deprotection of a protective group at the 3'-position of the compounds of formula (III). This means that the compounds of formula (I), which are important intermediates to be converted into 3'-azido-3'-deoxythymidine and its related compounds, can be easily made and also that the compounds of formula (VIII), including 5-methyluridine, which is low-priced and is easy to obtain in large amounts, can be used as starting materials.

The conversion of the compound of formula (I) into the compound of formula (VII) according to the present invention comprises reductive removal of the 2'-position halogen from the compound of formula (I) to give the compound of formula (IV), substitution of the 3'-substituent of the compound of formula (IV) by a leaving group such as a sulfonyl group, a halogen group or the like, conversion of the resulting compound into its 2,3'-anhydride, and introduction of an azido group or the like into its 3'-position by the use of a nucleophilic reagent to give the compound of formula (VII), such as 3'-azido-3'-deoxythymidine.

The reductive removal of the 2'-position halogen from the compound of formula (I) to give the compound of formula (IV) may be achieved by reduction with a hydrogen donor in the presence of a palladium catalyst or a nickel catalyst. As the palladium catalyst and the nickel catalyst to be used for reducing the compound of formula (I) to the compound of formula (IV), for example, mentioned are from 5 to 20% palladium-carbon, palladium-barium sulfate, palladium-barium carbonate, and Raney nickel. As the hydrogen donor, suitable are cyclohexene, hydrazine, 1,4-cyclohexadiene, formic acid, ammonium formate, hydrogen gas, etc. When hydrogen gas is used, in general, the pressure in the reaction system is somewhat elevated, but ordinary pressure may also be employed with no problem. The reaction may be effected in ordinary solvents. For instance, suitable are alcohols such as methanol, ethanol, etc. as well as acetonitrile, water, dimethylformamide, etc., and mixed solvents of these. The reaction may be effected in the presence of a salt. As suitable salts, for example, mentioned are sodium acetate, ammonium acetate, ammonium formate, sodium carbonate, etc.

The reaction is effected, in general, at temperatures falling within the range of from −40° C. to +60° C., preferably 0° to 20° C., for 1 to 48 hours, preferably 2 to 24 hours. After the reaction has finished, the catalyst is filtered from the reaction mixture, and the reaction mixture is concentrated to be directly used in the next reaction step, without isolating the product formed therefrom. If, however, the product is desired to be isolated from the reaction mixture, any ordinary method may be employed. For instance, the catalyst may be removed from the reaction mixture by filtration, the reaction mixture may be concentrated, the resulting residue may be dissolved in water, and the aqueous solution thus-formed may be extracted with an organic solvent such as ethyl acetate, etc.

If desired, the compound of formula (I) as produced from the compound of formula (III) may be directly subjected to the present reduction without isolating it. For instance, an acid such as formic acid or acetic acid is added to neutralize the base that was used in the previous reaction step to form a salt, and a palladium catalyst or a nickel catalyst is added to the reaction system to effect the intended reduction to give the compound of formula (IV).

To convert the compound of formula (IV) into the compound of formula (V), the former is reacted with a sulfonyl halide in the presence of a basic catalyst such as pyridine, etc. in a basic solvent. Preferred sulfonyl halides include toluenesulfonyl chloride, methanesulfonyl chloride, and trifluoromethanesulfonyl chloride. To isolate the compound of formula (V) thus formed, the base is neutralized with an acid such as hydrochloric acid, etc. or with an ion-exchanging resin, if a basic catalyst was used, then the reaction mixture is concentrated and thereafter it is subjected to ordinary extraction with an organic solvent such as ethyl acetate, etc. to isolate the intended compound. After the reaction, if desired, the reaction mixture may be directly subjected to the next reaction without isolating the product therefrom.

To convert the compound of formula (V) into the compound of formula (VI), the former is subjected to ring-closure in the presence of a base. As the base to be used for the ring-closure, for example, mentioned are sodium hydroxide, potassium hydroxide, ammonia, sodium methylate, potassium phthalimide, etc. The amount of the base to be used may be selected from the range of from 1 to 10, preferably 1 to 5, molar equivalents relative to the compound of formula (V). The reaction temperature for the ring-closure may be selected from the range of from −40° C. to +60° C., preferably 0° to 20° C. After the reaction, the compound of formula (VI) may be isolated by conventional methods.

To convert the compound of formula (VI) into the compound of formula (VII), the former is subjected to ring-cleavage with an azide, a cyanide or a fluoride. As the azide to be used for the reaction, for example, mentioned are alkali metal azides such as sodium azide, lithium azide, etc., as well as ammonium azide, trimethylsilyl azide, etc. As the cyanide to be used for the reaction, for example, mentioned are alkali metal cyanides such as sodium cyanide, lithium cyanide, etc. As the fluoride to be used for the reaction, for example, mentioned are hydrogen fluoride, lithium fluoride, potassium fluoride, tetrabutylammonium fluoride, diethylaminosulfato trifluoride, etc. The reaction is effected in a solvent capable of dissolving both the compound of formula (VI) and the azide, cyanide or fluoride. As the solvent suitable for the reaction, for example, mentioned are dimethylformamide, dimethylsulfoxide, etc.

The 5'-position protective group may be removed at any desired stage of the conversion of the compound of formula (V) to the compound of formula (VII), by a suitable method. For example, if $R^1$ represents a hydrocarbon group having 1 to 19 carbon atoms, for example, a methyl group, an ethyl group, an isopropyl group, a benzyl group, trityl group, etc., the protective group may be removed by cleavage optionally using boron tribromide, hydrogen bromide, trimethylsilyl iodide, formic acid, trifluoroacetic acid, etc., or hydrogenation optionally using a catalyst such as palladium, platinum, etc.

If $R^1$ represents an acyl group having 1 to 7 carbon atoms, for example, an acetyl group, a benzoyl group, etc., the protective group may be removed by saponification optionally using a base, e.g., alkali such as sodium hydroxide, potassium hydroxide, etc., a carbonate such as potassium carbonate, potassium bicarbonate, etc., a cyanide such as potassium cyanide, etc., ammonia and their salts, etc.

If $R^1$ represents an organic silyl group, for example, a trimethylsilyl group, a t-butyldimethylsilyl group, etc., the protective group may be removed by acid hydrolysis optionally using an acid or fluoride, e.g., hydrogen chloride, hydrogen fluoride, acetic acid, citric acid, tetrabutylammonium fluoride, etc.

The above reactions are effected, in general, at temperatures falling within the range of from −40° to +120° C., preferably 0° to 20° C., for 0.1 to 48 hours, in a solvent optionally selected from alcohols such as methanol, ethanol, etc., acetonitrile, tetrahydrofuran, demethylformamide, dichloromethane, chloroform, water, etc. The compound of formula (VII), such as typically 3'-azido-3'-deoxythymidine, may be isolated from the reaction mixture by an ordinary purifying method, for example, by purification with adsorbing resins or by crystallization.

Other features of the invention will become apparent in the course of the following descriptions of exemplary embodiments which are given for illustration of the invention and are not intended to be limiting thereof.

EXAMPLES

Reference Example 1

Production of 2'-deoxy-2'-bromo-3',5'-O-diacetyl-5-methyluridine from 5-methyluridine:

42.5 g (350 mmol) of trimethyl orthoacetate were added to 125 ml of a slurry of acetic acid containing 75.3 g (250 mmol) of 85.7% purity 5-methyluridine and reacted at 50° C. for one hour. The reaction mixture was concentrated under reduced pressure to obtain 2',3'-O-methoxyethylidene-5-methyluridine. To the thus-obtained 2',3'-O-methoxyethylidene-5-methyluridine, were added 207 ml of acetonitrile. The resulting solution was heated to 50° C., and a mixture comprising 202 g (3 equivalents) of 30% hydrogen bromide/acetic acid and 30.8 g (one equivalent) of acetic acid bromide was dropwise added thereto over a period of 2 hours. The reaction mixture was heated to 60° C. and reacted for a further 4 hours. The reaction mixture was then cooled to 10° C., and 125 ml of water were added thereto. Then, the reaction mixture was neutralized with an aqueous 25% sodium hydroxide solution, and the acetonitrile layer was separated. The aqueous layer was extracted with acetonitrile. The organic layers were combined and concentrated under reduced pressure. The resulting residue was recrystallized from methanol to obtain 71.5 g (176 mmol) of 2'-deoxy-2'-bromo-3', 5'-O-diacetyl-5-methyluridine. Its yield was 70.6%, based on 5-methyluridine.

NMR Analysis ($^1$H, CDCl$_3$)

δ 1.95 (3H, s, 5 Me), 2.16 (3H, s, 5' OAc), 2.19 (3H, s, 3' OAc), 4.39 (3H, m, 5' H+4' H), 4.54 (1H, dd, J=6.0, 6.0 Hz, 2' H), 5.18 (1H, dd, J=6.0, 3.7 Hz, 3' H), 6.23 (1H, d, J=6.0 Hz, 1' H), 7.19 (1H, q, J=1.8 Hz, 6 H), 8.70 (1H, br, 3 NH).

Example 1

Production of 2'-deoxy-2'-bromo-5'-O-acetyl-5-methyluridine from 2'-deoxy-2'-bromo-3', 5'-O-diacetyl-5-methyluridine:

400 ml of acetonitrile and 2.16 g (3 equivalents) of water were added to 16.2 g (40.0 mmol) of 2'-deoxy-2'-bromo-3', 5'-O-diacetyl-5-methyluridine, and the mixture was stirred. The resulting solution was cooled to 0° C., 6.01 g (3 equivalents) of hydrazine monohydrate were added thereto, and the mixture was reacted for 20 hours at that temperature. 100 ml of water were added to the reaction mixture, which was then neutralized to a pH of 6.8 by adding 6 N-hydrochloric acid thereto. The acetonitrile layer was separated, washed with saturated saline solution, dried with anhydrous magnesium sulfate, and then concentrated under reduced pressure to obtain 13.5 g of 2'-deoxy-2'-bromo-5'-O-acetyl-5-methyluridine. Its purity was 81.8%. Its yield was 76.0%.

NMR Analysis ($^1$H, CDCl$_3$):

δ 1.95 (3H, s, 5 Me), 4.22 (1H, t, J=5.0 Hz, 4' H), 4.32–4.46 (3H, m, 5' H+3' H), 4.53 (1H, t, J=5.4 Hz, 2' H), 6.18 (1H, d, J=5.4 Hz, 1' H), 7.26 (1H, bs, 6 H), 9.05 (1H, bs, 3 NH).

NMR Analysis ($^{13}$C, CDCl$_3$):

δ 12.71, 20.90, 43.89, 63.19, 70.28, 81.67, 90.43, 111.64, 116.52, 135.10, 170.36

IR Spectral Analysis (KBr):

cm$^{-1}$ 3434, 3075, 1670, 1471, 1385, 1272, 1236, 1092, 1042, 784, 565, 490

UV Spectral Analysis (H$_2$O):

λ$^{max}$ 261.6 nm

Mass Spectral Analysis (FAB Mode)

calculated (M$^+$H$^+$, C$_{12}$H$_{16}$O$_6$N$_2$Br): 363.0192 measured: 363.0193

Example 2

Production of 2'-deoxy-2'-bromo-5'-O-acetyl-5-methyluridine from 2'-deoxy-2'-bromo-3, 5',5-O-diacetyl-5-methyluridine:

10 ml of acetonitrile were added to 405 mg (1.0 mmol) of 2'-deoxy-2'-bromo-3',5'-O-diacetyl-5-methyluridine, and the mixture was stirred. The resulting solution was cooled to 0° C., 100 mg (2 equivalents) of hydrazine monohydrate were added thereto, and the mixture was reacted for 17.8 hours at that temperature. The reaction solution was subjected to HPLC analysis, which showed the production of 84.1% of 2'-deoxy-2'-bromo-5'-O-acetyl-5-methyluridine, based on the HPLC area.

Example 3

Production of 2'-deoxy-2'-bromo-5'-O-acetyl-5-methyluridine from 2'-deoxy-2'-bromo-3',5'-O-diacetyl-5-methyluridine:

10 ml of acetonitrile were added to 405 mg (1.0 mmol) of 2'-deoxy-2'-bromo-3',5'-O-diacetyl-5-methyluridine, and the mixture was stirred. The resulting solution was cooled to 0° C., 100 mg (2 equivalents) of hydrazine monohydrate and 90 mg (5 equivalents) of water were added thereto, and the mixture was reacted for 18.3 hours at that temperature. The reaction solution was subjected to HPLC analysis, which showed the production of 84.9% of 2'-deoxy-2'-bromo-5'-O-acetyl-5-methyluridine, based on the HPLC area.

Example 4

Production of 2'-deoxy-2'-bromo-5'-O-acetyl-5-methyluridine from 2'-deoxy-2'-bromo-3',5'-O-diacetyl-5-methyluridine:

10 ml of acetonitrile were added to 405 mg (1.0 mmol) of 2'-deoxy-2'-bromo-3',5'-O-diacetyl-5-methyluridine, and the mixture was stirred. The resulting solution was cooled to 0° C., 150 mg (3 equivalents) of hydrazine monohydrate and 90 mg (5 equivalents) of water were added thereto, and the mixture was reacted for 2.1 hours at that temperature. The reaction solution was subjected to HPLC analysis, which showed the production of 71.3% of 2'-deoxy-2'-bromo-5'-O-acetyl-5-methyluridine, based on the HPLC area.

Example 5

Production of 2'-deoxy-2'-bromo-5'-O-acetyl-5-methyluridine from 2'-deoxy-2'-bromo-3',5'-O-diacetyl-5-methyluridine:

20 ml of methanol were added to 810 mg (2.0 mmol) of 2'-deoxy-2'-bromo-3',5'-O-diacetyl-5-methyluridine, and the mixture was stirred. The resulting solution was cooled to 0° C., 405 mg (2 equivalents) of triethylamine were added thereto, and the reaction solution was warmed up to room temperature and reacted for 5 days at room temperature. The reaction solution was subjected to HPLC analysis, which showed the production of 96.3% of 2'-deoxy-2'-bromo-5'-O-acetyl-5-methyluridine, based on the HPLC area.

Example 6

Production of 5'-O-acetylthymidine from 2'-deoxy-2'-bromo-5'-O-acetyl-5-methyluridine:

12.47 g (28.1 mmol) of 2'-deoxy-2'-bromo-5'-O-acetyl-5-methyluridine were dissolved in 240 ml of methanol, and 6.91 g (3 equivalents) of sodium acetate were added thereto. To the reaction mixture, were added 1.25 g of 5% palladium-barium sulfate catalyst (0.1 equivalent). Then, the reaction system was filled with hydrogen gas and reacted for 24 hours at room temperature. The catalyst was removed from the reaction mixture, 100 ml of water were added, and the reaction mixture was neutralized to have a pH of 7.0 by adding an aqueous 25% sodium hydroxide solution thereto. The resulting solution was concentrated to about 100 ml, sodium chloride was added thereto until saturation, and the thus-saturated solution was extracted with ethyl acetate. The thus-extracted organic layer was washed with saturated saline solution, dried with anhydrous magnesium sulfate, and then concentrated under reduced pressure to obtain white crystals. The crystals were washed with a small amount of methylene chloride to obtain 3.04 g (10.7 mmol) of 5'-O-acetylthymidine. Its yield was 38.1%.

NMR Analysis ($^1$H, CDCl$_3$):

δ 1.94 (3H, d, J=1.4 Hz, 5 Me), 2.18 (1H, m, 2 H'α), 2.43 (1H, ddd, J=4.5, 6.2, 13.5 Hz, 2'Hβ), 4.13 (1H, q, J=4.5 Hz, 4'H), 4.30 (1H, dd, J=3.5, 12.3 Hz, 5' Hα), 4.39 (1H, m, 3'H), 4.40 (1H, dd, J=4.5, 12.3 Hz, 5' Hβ), 6.27 (1H, t, J=6.5 Hz, 1' H), 7.27 (1H, q, J=1.4 Hz, 6H), 8.21 (1H, bs, 3 NH)

Example 7

Production of 5'-O-acetylthymidine from 2'-deoxy-2'-bromo-3',5'-O-diacetyl-5-methyluridine:

20.26 g (50.0 mmol) of 2'-deoxy-2'-bromo-3',5 ',-O-diacetyl-5-methyluridine were dissolved in 500 ml of acetonitrile. This solution was cooled to 0° C., and 5.01 g (2 equivalents) of hydrazine monohydrate were added thereto to start the reaction therebetween. After 11 hours, 9.21 g (4 equivalents) of formic acid, 3.34 g of 10% palladium-carbon catalyst (water content of 60.7%; 0.1 weight equivalent) and 250 ml of methanol were added thereto, and the reaction system was filled with hydrogen gas to again start the reaction at room temperature. After 14 hours, the catalyst was removed from the reaction mixture by filtration, and the reaction liquid was concentrated under reduced pressure. The resulting residue was dissolved in water and extracted with ethyl acetate, and the thus extracted organic layer was washed with saturated saline solution. The organic layer was dried with anhydrous magnesium sulfate and then concentrated under reduced pressure to obtain 27.3 g of 5'-O-acetylthymidine. The product was used in the next reaction, without being purified.

Example 8

Production of 5'-O-acetyl-3'-O-methanesulfonylthymidine from 5'-O-acetylthymidine:

The 5'-O-acetylthymidine obtained in Example 7 was dissolved in 100 ml of pyridine and cooled to 0° C. Then, 11.57 g (2 equivalents) of methanesulfonyl chloride were added thereto. After these were reacted at 0° C. for 1.5 hours, 5.79 g (one equivalent) of methanesulfonyl chloride were added thereto and reacted at 0° C. for 1.5 hours. The reaction mixture was concentrated under reduced pressure, the residue was dissolved in methylene chloride, and the insoluble substances were removed by filtration. The organic layer was washed with water; aqueous, saturated sodium hydrogencarbonate solution; water; and saturated saline solution in this order, dried with anhydrous sodium sulfate and concentrated under reduced pressure to obtain 10.4 g of 5'-O-acetyl-3'-O-methanesulfonylthymidine. The product was used in the next reaction, without being isolated.

NMR Analysis ($^1$H, CDCl$_3$):

δ 1.94 (3H, d, J=1.1 Hz, 5 Me), 2.13 (3H, s, 5' OAc), 2.33 (1H, ddd, J=6.9, 8.3, 14.7 Hz, 2'Hα), 2.68 (1H, ddd, J=2.9, 6.0, 14.7 Hz, 2' Hβ), 3.12 (3H, s, 3' OMs), 4.37 (2H, m, 5' H), 4.44 (1H, m, 4' H), 5.27 (1H, ddd, J=2.9, 5.7, 6.9 Hz, 3' H), 6.26 (1H, dd, J=6.0, 8.3 Hz, 1' H), 7.20 (1H, d, J=1.1 Hz, 6H), 8.85 (1H, bs, 3 NH)

Example 9

Production of 3'-azido-3'-deoxythymidine from 5'-O-acetyl-3'-O-methanesulfonylthymidine:

100 ml of ethanol were added to 10.4 g of 5'-O-acetyl-3'-O-methanesulfonylthymidine obtained in the previous step, and the mixture was heated under reflux. To the resulting solution, a solution prepared by dissolving 1.15 g (one equivalent) of sodium hydroxide in 10 ml of water, was added dropwise over a period of 45 minutes. This was heated for a further 45 minutes, then cooled to room temperature, and concentrated under reduced pressure. The resulting residue was dissolved in 50 ml of dimethylformamide, 2.11 g (1.5 equivalents) of lithium azide were added thereto, and the mixture was reacted at 120° C. for 16.5 hours. The reaction solution was cooled to room temperature and subjected to HPLC analysis, which showed the production of 3.21 g (12.0 mmol) of azidothymidine. Its yield was 24.0%, based on 2'-deoxy-2'-bromo-3',5'-O-diacetyl-5-methyluridine.

As is obvious from the above-mentioned description, useful nucleoside derivatives, such as AZT, and their intermediates may be produced from low-cost starting materials such as 5-methyluridine, according to the present invention. Therefore, the present invention is extremely useful in an industrial setting.

The present application is based on Japanese Patent Application Nos. 193332/1993 and 180109/1994, which are incorporated herein by reference.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A compound of formula (I):

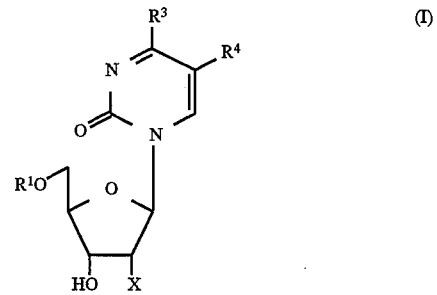

wherein X represents a halogen atom; $R^1$ represents an acyl group having 1 to 7 carbon atoms $R^3$ represents a hydroxyl group, a protected hydroxyl group, amino group, or a protected amino group; and represents a hydrocarbon group having 1 to 12 carbon atoms, a hydrogen atom or a halogen atom.

2. The compound of claim 1 having formula (II):

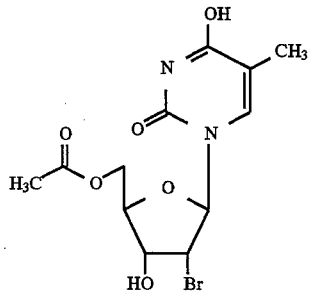

wherein x represents bromine; $R^1$ represents acetyl group; $R^3$ represents hydroxyl group; and $R^4$ represents methyl group.

3. A method for producing a compound of formula (I):

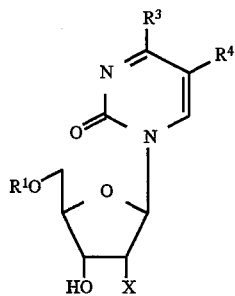

wherein X represents a halogen atom; $R^1$ represents an acyl group having 1 to 7 carbon atoms; $R^3$ represents a hydroxyl group, a protected hydroxyl group, an amino group, or a protected amino group; and $R^4$ represents a hydrocarbon group having 1 to 12 carbon atoms, a hydrogen atom or a halogen atom, said process comprising reacting a compound of formula (III):

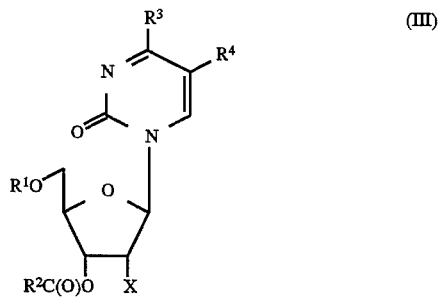

wherein X represents a halogen atom; $R^1$ represents an acyl group having 1 to 7 carbon atoms; $R^2$ represents an alkyl group having 1 to 6 carbon atoms; $R^3$ represents a hydroxyl group, a protected hydroxyl group, an amino group, or a protected amino group; and $R^4$ represents a hydrocarbon group having 1 to 12 carbon atoms, a hydrogen atom or a halogen atom, with a base selected from the group consisting of hydrazine monohydrate and triethylamine.

4. The method of claim 3, wherein said base is hydrazine monohydrate.

5. The method of claim 3, wherein said base is triethylamine.

* * * * *